United States Patent
Chung et al.

(10) Patent No.: US 8,637,279 B2
(45) Date of Patent: Jan. 28, 2014

(54) **RECOMBINANT *ESCHERICHIA COLI* PRODUCING D-XYLONIC ACID FROM D-XYLOSE AND METHOD FOR PRODUCING D-XYLONIC ACID USING THE SAME**

(75) Inventors: Wook-Jin Chung, Seongnam-si (KR); Huaiwei Liu, Yongin-si (KR); Kris Niño Gomez Valdehuesa, Yongin-si (KR); Kristine Rose Medina Ramos, Yongin-si (KR); Mi-Deok Han, Seoul (KR)

(73) Assignee: Myongji University Industry and Academia Cooperation Foundation, Gyeonggi-do (KR)

( * ) Notice: Subject to any disclaimer, the term of this patent is extended or adjusted under 35 U.S.C. 154(b) by 0 days.

(21) Appl. No.: 13/590,582

(22) Filed: Aug. 21, 2012

(65) Prior Publication Data

US 2013/0084612 A1    Apr. 4, 2013

(30) Foreign Application Priority Data

Sep. 30, 2011  (KR) .................. 10-2011-0100117

(51) Int. Cl.
*C12N 1/20* (2006.01)
(52) U.S. Cl.
USPC ..................................... 435/137; 435/252.33
(58) Field of Classification Search
USPC ............................................ 435/137, 252.33
See application file for complete search history.

(56) References Cited

FOREIGN PATENT DOCUMENTS

WO     2010/106230     9/2010

OTHER PUBLICATIONS

Huaiwei Liu, Kris Nino G. Valdehuesa, Grace M. Nisola, Kristine Rose M. Ramos, Wook-Jin Chung. High yield production of D-xylonic acid from D-xylose using engineered *Escherichia coli*. Bioresource Technology. 115:244-248, 2012, Available online on Aug. 22, 2011.*

J.Buchert et al., "Production of Xylonic Acid by *Pseudomonas fragi*", Biotechnology Letters, Jul. 9, 1986, 541-546, vol. 8 No. 8.

Mervi H. Toivari et al, "Microbial D-Xylonate Production", Appl Microbiol Biotechnol, Aug. 9, 2012, Springer.

Toivari, M., et al., Metabolic engineering of *Saccharomyces* for bioconversion of D-xylose to D-xylonate, Metab. Eng., (2012).

Yvonne Nygard et al., "Bioconversion of D-xylose to D-xylonate with *Kluyveromyces lactis*", (2011) Elsevier Inc.

Mervi H. Toivari et al, "*Saccharomyces cerevisiae* engineered to produce D-xylonate", Appl Microbiol Biotechnol, Aug. 3, 2010, Springer.

* cited by examiner

*Primary Examiner* — Tekchand Saidha
*Assistant Examiner* — Rama P Ramanujam
(74) *Attorney, Agent, or Firm* — Renner, Otto, Boisselle & Sklar, LLP

(57) ABSTRACT

Disclosed herein is a recombinant *Escherichia coli* (*E. coli*) capable of producing D-xylonic acid from D-xylose and a method for producing D-xylonic acid using the same. The recombinant *E. coli* producing D-xylonic acid from D-xylose according to the present invention is a recombinant *E. coli* EWX4 (Microorganism deposition number KCTC11988BP) capable of producing D-xylonic acid from D-xylose. When utilizing the recombinant *E. coli* prepared by the method of the present invention, it is possible to produce D-xylonic acid from D-xylose with high yield while reducing production cost using sole carbon source.

1 Claim, 5 Drawing Sheets a: D-xylose isomerase (*E. coli*)
b: D-xylulose kinase (*E. coli*)
c: D-xylonate dehydratase (*E. coli*)
d: Aldolase (*E. coli*)
e: D-xylose dehydrogenase (*C. crescentus*)

RECOMBINANT ESCHERICHIA COLI PRODUCING D-XYLONIC ACID FROM D-XYLOSE AND METHOD FOR PRODUCING D-XYLONIC ACID USING THE SAME

CROSS-REFERENCE TO RELATED APPLICATION

This application claims the benefit of Korean Patent Application No. 10-2011-0100117, filed on Sep. 30, 2011 in the Korean Intellectual Property Office, the disclosures of which are incorporated herein by reference.

BACKGROUND

1. Technical Field

The present invention relates to a recombinant *Escherichia coli* (*E. coli*) capable of producing D-xylonic acid from D-xylose and a method for producing D-xylonic acid using the same. More particularly, the present invention relates to a method for engineering *E. coli* capable of producing D-xylonic acid from D-xylose by disrupting the genes responsible for the metabolism of D-xylose and D-xylonic acid in wild type *E. coli*, and introducing a necessary gene originating heterologous bacteria, and to a method for producing D-xylonic acid from D-xylose using the engineered *E. coli* by the method.

2. Description of the Related Art

It is now commonly accepted that the world must shift from dependence upon fossil fuels to biomass-based fuels to combat global warming. Numerous scientists have devoted themselves to biofuel research. Compared with biofuels, research on bio-sourced chemicals and materials traditionally derived from fossils has not attracted much interest until the last decade. Biomass processing has come to the forefront of both biological and chemical engineering research.

To support the campaign on the integrated conversion of biomass, the US Department of Energy (DOE) identified 30 chemicals which could be used for the productions of high value-added chemicals in 2004. As one of the top 30 value-added chemicals, D-xylonic acid has found applications in many fields. For example, it has been utilized as a substrate for biosynthesis of 1,2,4-butanetriol. Further, it has been known that D-xylonic acid can be used as a concrete additive which improves concrete dispersion. In addition, D-xylonic acid has been reported in the fields of foods, pharmaceuticals and agriculture.

D-xylonic acid can be produced from D-xylose by microbial conversion. Bacteria such as *Pseudomonas, Gluconobacter* and *Caulobacter* are capable of producing dehydrogenase for converting D-xylose to D-xylonolactone, which can be hydrolyzed naturally or by an enzyme to produce D-xylonic acid.

D-xylose dehydrogenase is also found in the fungus *Hypocrea jecorina*, but its function reminas unclear. Recently, two recombinant yeast strains have been constructed aiming to produce D-xylonic acid from lignocellulosic hydrolysates.

But so far, no commercial production method of D-xylonic acid has been established. Reasons are either because bacteria strains produce many other oxidizing enzymes resulting in the conversion of other sugars present in lignocellulosic hydrolysates or because the engineered yeast strains have low D-xylonic acid accumulation rate and yield. In addition, high cost of peptone and yeast extract as nitrogen sources in the media is generally uneconomical for industrial scale production of D-xylonic acid.

BRIEF SUMMARY

The present invention is directed to *Escherichia coli* (*E. coli*) producing D-xylonic acid from D-xylose and a method for producing D-xylonic acid by culturing *E. coli* at laboratory or industrial scale at low cost.

In accordance with one aspect, the present invention provides a recombinant *E. coli* EWX4 (Microorganism deposition number KCTC11988BP) capable of producing D-xylose acid from D-xylose.

In accordance with another aspect, the present invention provides a method for producing a recombinant *E. coli* EWX4 (Microorganism deposition number KCTC11988BP) capable of producing D-xylonic acid from D-xylose by introducing D-xylose dehydrogenase gene of *Caulobacter crescentus* into *E. coli*.

The method comprises the steps of:
- disrupting yagF and yjhG genes encoding D-xylonic dehydratase in *E. coli* to manufacture *E. coli* ΔyagFΔyjhG (Step a);
- disrupting xylA gene encoding D-xylose isomerase and xylB gene encoding xylulose kinase in *E. coli* ΔyagFΔyjhG to Manufacture *E. coli* ΔxylABΔyagFΔyjhG (Step b); and
- introducing D-xylose dehydrogenase gene of *Caulobacter crescentus* (*C. crescentus*) into *E. coli* ΔxylABΔyagFΔyjhG (Step c).

*E. coli* in Step a can be *E. coli* W3110 (ATCC Number 27325).

In Step a, the yagF gene and yjhG gene may be disrupted sequentially.

In accordance with a further aspect, the present invention provides a method for producing D-xylonic acid from D-xylose using recombinant *E. coli* prepared by the method according to the present invention.

When utilizing the recombinant *E. coli* prepared by the method according to the present invention, it is possible to produce D-xylonic acid from D-xylose at high yield while reducing production cost using a sole carbon source.

BRIEF DESCRIPTION OF THE DRAWINGS

The above and other aspects, features and advantages of the invention will become apparent from the following description of exemplary embodiments given in conjunction with the accompanying drawings, in which.

DETAILED DESCRIPTION

Figure 1:
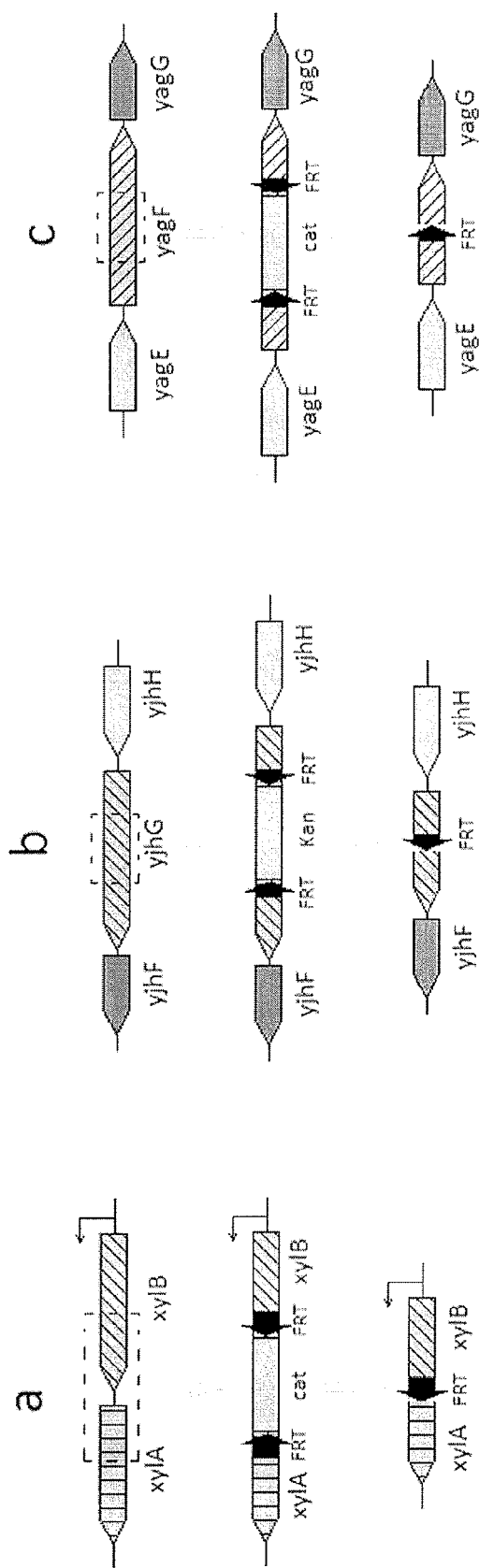
FIG. 1 shows a disruption procedure and gene structure mutation of *E. coli* according to the present invention.

The present invention will be described in more detail with reference to some examples, but it should be understood that the present invention is not limited thereto.

EXAMPLE 1

Strains and Strain Construction

First, a method for engineering *E. coli* producing D-xylonic acid from D-xylose will be described and then a method for producing D-xylonic acid by culturing the engineered *E. coli* will be described.

The method for engineering *E. coli* mainly comprises two procedures.

One is to disrupt specific genes in *E. coli* and the other is to introduce D-xylose dehydrogenase of *C. crescentus*.

First of all, the gene disruption procedure in wild type *E. coli* is described. As D-xylose and D-xylonic acid metabolizing involved genes among the chromosomal genes in wild type *E. coli*, xylA gene (SEQ ID. NO: 1) and xylB gene (SEQ ID. NO: 2) encode D-xylose isomerase and xylulose kinase, respectively. In addition, yagF gene (SEQ ID NO: 3) and yjhG gene (SEQ ID. NO: 4) encode D-xylonic dehydratase.

Gene inactivation strategy was applied to disrupt the chromosomal genes in wild type *E. coli*. Plasmid pKD46 was used as the Red recombinase expression vector. pKD3 and pKD4 were used as template plasmids for the PCR amplification of disruption cassettes. In addition, pCP20 was used as the resistance-gene eliminating plasmid.

Primer pairs used for gene disruptions are listed in Table 1.

For the construction of *E. coli* ΔxylABΔyagFΔyjhG wherein xylA and xylB genes were disrupted, xylAB disruption was conducted in *E. coli* ΔyagFΔyjhG in the same way as described above.

PCR verifications were conducted after each disruption with primer pairs corresponding to up- and downstream of disrupted regions. For multiple gene disruptions, former disruptions were verified simultaneously to check for incorrect recombination between FRT sites.

As mentioned above, after the gene disruption procedure in a specific gene in wild type *E. coli*, D-xylose dehydrogenase of *C. crescentus* (SEQ ID. NO: 11) was introduced.

A λDE3 Lysogenization Kit was used to integrate λDE3 prophage into the *E. coli* host chromosome. Lysogens were verified using the T7 tester phage according to the user protocol TB0B.

The nucleotide sequence of D-xylose dehydrogenase of *C. crescentus* was synthesized directly and ligated into NdeI-BamHI-linearized vector pET28a.

The final construct was denoted as pET28a-cxylB and electrotransformed into λDE3 lysogens.

In accordance with the above method, various types of engineered *E. coli* of the present invention were prepared. The sorts of *E. coli* are listed in Table 2.

TABLE 1

| Primers | Base sequence (5'-3') | Function | SEQ ID. NO: |
|---|---|---|---|
| KxylAB-F | TCGTGAAGGTTACGAAACGCTGTTAAATACCGACTxylAB<br>TGCGTCATATGAATATCCTCCTTAGT | xylAB disruption cassette | 5 |
| KxylAB-R | CGGCTCATGCCGCTGAACCCATAGCAATTTAGGCG<br>CAGTAGTGTAGGCTGGAGCTGCTTCG | | 6 |
| KyihG-F | GTGCAAACCATTGGCGCACGCTTCGCCAATGGCGAyjhG<br>ATTATGTGTAGGCTGGAGCTGCTTCG | yjhG disruption cassette | 7 |
| KyjhG-R | CCTGATCGAGCAGGAGTTGCTTGAACCGCTGACGC<br>CGTTCCATATGAATATCCTCCTTAGT | | 8 |
| KyagF-F | CGCCACCATGATTGCGCTGGCCGCGATGCACGACCyagF<br>TGCCGATATGAATATCCTCCTTAGT | yagF disruption cassette | 9 |
| KyagF-R | CCTGCTCGCGCAGGCACTGGCGGAAGCGCGCCCGG<br>CGCTC | | 10 |

For the construction of *E. coli* ΔxylAB wherein xylA and xylB genes are disrupted, xylAB disruption cassette was amplified with primers KxylAB-F and KxylAB-R using pKD3 as template. The disruption procedure and mutations of gene structure are illustrated in FIG. 1a.

For construction of *E. coli* ΔyagFΔyjhG wherein yagF and yjhG genes are disrupted, a two-step approach was conducted.

First, the yagF gene of wild type *E. coli* was disrupted with a PCR fragment, which was amplified with primers KyagF-F and KyagF-R using pKD4 as a template. Then, the yjhG gene in *E. coli* ΔyagF wherein yagF had been disrupted was disrupted with another PCR fragment, which was amplified with primers KyihG-F and KyihG-R using pKD3 as template. The mutations of gene structure are illustrated in FIGS. 1b and 1c.

TABLE 2

| Strain | Genotype/Characteristic | Resource |
|---|---|---|
| W3110 | Wild-type | ATCC No. 27325 |
| EWM1 | W3110ΔxylAB | Present invention |
| EWM2 | W3110ΔyagFΔyjhG | Present invention |
| EWM3 | W3110ΔxylABΔyagFΔyjhG | Present invention |
| EWX1 | W3110(DE3), pET28a-cxylB | Present invention |
| EWX2 | W3110(DE3)Δ xylAB, pET28a-cxylB | Present invention |
| EWX3 | W3110(DE3)ΔyagFΔyjhG, pET28a-cxylB | Present invention |
| EWX4 | W3110(DE3)ΔxylABΔyagFΔyjhG, pET28a-cxylB | Present invention |

*E. coli* EWX4 finally engineered using the above mentioned method was deposited at KCTC of KRIBB (Korean Collection for Type Culture of Korea Research Institute of Bioscience & Biotechnology) on Jun. 25, 2011 and the deposition number was KCTC 11988BP.

EXAMPLE 2

Media and Culture Conditions

MOPS minimal medium was used for solid growth test and small scale culture. For solid growth test, plates containing MOPS salt and 4 g/L carbon source (glucose, xylose, or xylonic acid) were streaked with overnight cultures, and incubated at 37° C. for 2 days.

For small scale cultures, 1.25 mL of overnight inoculant was transferred into a 100 ml Erlenmeyer flask containing 25 ml liquid medium, 4 g/L D-glucose, and 10 g/L D-xylose, and incubated at 37° C. with 180 rpm agitation. 0.5 mM IPTG was added to induce xylose dehydrogenase expression when the optical density at 600 nm ($OD_{600}$) reached 0.3 AU.

The strains were removed from the culture by centrifugation (2500 g for 10 minutes). D-xylonic acid containing the supernatant was then treated with activated carbon and vacuum concentrated from 1 L to 200 mL. EtOH (3:1, v/v) was added to the concentrate. After 12 hours at 4° C., the precipitated calcium xylonic acid was vacuum dried. The dried calcium xylonic acid product was analyzed by HPLC and $^{13}$C- and $^{1}$H-NMR. The NMR spectra were recorded on a Varian Unity Inova Spectrometer.

For large scale culture, fermentations were carried out in a 5 L laboratory fermenter. M9 minimal medium (3 L), containing 10 g/L D-glucose and 40 g/L D-xylose, was used. Prior to fermentation, contamination was prevented by addition of 40 mg/L of kanamycin. Inoculants were prepared by culturing strains in 150 mL LB medium at 37° C. agitated at 180 rpm for 12 hours, and then transferred into the fermenter.

In the fermenter, cultivation was conducted at a temperature of 37° C., stirring at 650 rpm, and airflow at 0.5 L/L/min. When $OD_{600}$ reached 10 AU, 0.5 mM IPTG was added with temperature decreased to 34° C., while the agitation speed was controlled by PID to maintain the dissolved oxygen (D.O.) at 20% air saturation.

To maintain the expression of D-xylose dehydrogenase during the fermentation, IPTG was periodically added every 24 hour. The feed of glucose was carried out by hand in order to maintain the growth of strains until the end of fermentation. Broth forming was controlled by addition of an antifoaming agent. The pH was maintained at 7.0 throughout the entire fermentation run by the addition of 2N $H_2SO_4$ and base solution. The base solution is 30% $NH_4OH$ for growth test or 30% $CaCO_3$ for D-xylonic acid purification.

EXAMPLE 3

Block of D-Xylose and D-Xylonic Acid Metabolic Pathways in E. coli W3110 in which Gene Disruption was Conducted E. coli W3110 (EWM1, EWM2 and EWM3 strains) wherein gene disruption was performed and wild type E. coli W3110 were cultured in accordance with Example 1. The results are summarized in FIG. 2.

Figure 2:
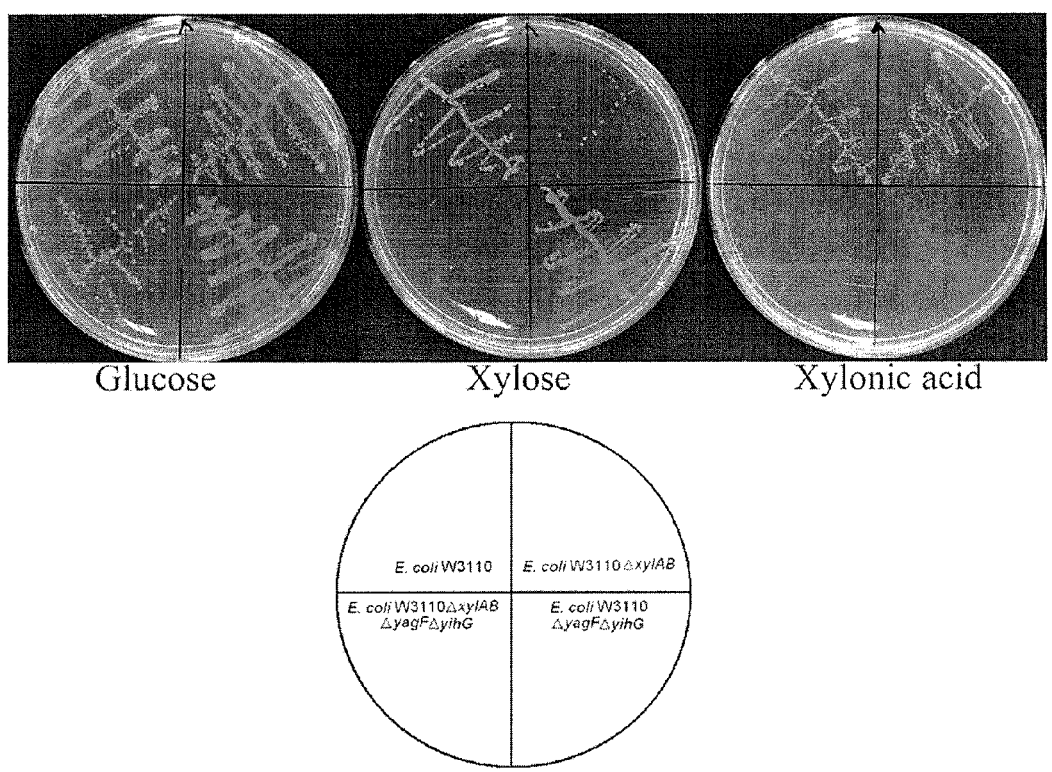
FIG. 2 shows the result of cultivation of *E. coli* W3110 (EWM1, EWM2 and EWM3 strains), genes of which are disrupted in Example 1 of the present invention, and wild type *E. coli* W3110.

According to FIG. 2, the native D-xylose catabolic pathway was blocked by disrupting the D-xylose isomerase and D-xylulose kinase genes (xylA and xylB) in E. coli W3110 chromosome.

The endogeneous D-xylonic catabolic pathway was blocked by disrupting two D-xylonic acid dehydratase genes (yagF and yjhG) in order to prevent D-xylonic acid consumption.

Solid growth tests proved that the xylose metabolism-blocked strain W3110ΔxylAB became incapable of consuming D-xylose. On the other hand, the xylonic acid metabolism-blocked strain W3110ΔyagFΔyjhG has lost its capability of consuming D-xylonic acid. Further, it was found that the double-blocked strain W3110ΔxylAB ΔyagFΔyjhG has lost capability of consuming both D-xylose and D-xylonic acid.

EXAMPLE 4

Comparison of D-Xylonic Acid Productivities of E. coli W3310 in Which the Xylose Dehydrogenase Gene of C. crescentus was Introduced The strains of E. coli W3110 (EWX1, EWX2 and EWX3 strains) to which the xylose dehydrogenase gene of C. crescentus was introduced were cultured in accordance with Example 1 and then productivities were compared. The results are summarized in Table 3 and FIG. 3.

TABLE 3

| Strain | Enzyme activity (U $mg^{-1}$) | D-xylonic acid concentration (g/L) | D-xylonic acid productivity (mg $L^{-1}h^{-1}$) | D-xylose consumption rate (mg $L^{-1}h^{-1}$) | D-xylonic acid yield (g [g D-xylose]$^{-1}$) |
|---|---|---|---|---|---|
| EWX1 | 3.86 | 4.44 | 73.95 | 78.30 | 0.44 |
| EWX2 | 4.00 | 4.68 | 77.97 | 72.45 | 0.47 |
| EWX3 | 3.61 | 3.81 | 63.50 | 90.98 | 0.38 |
| EWX4 | 3.79 | 5.05 | 84.23 | 91.17 | 0.51 |

The wild type strain of E. coli W3110 was incapable of producing D-xylonic acid from D-xylose. To construct the D-xylonic acid producing strains, the xylose dehydrogenase gene of C. crescentus (cxylB) (SEQ ID NO: 11) was ligated into the expression vector pET28a, and then transformed into E. coli W3110 and its pathway-blocked mutants.

Each of cxylB expressing strain was cultured in MOPS minimal medium containing 4 g/L D-glucose and 10 g/L D-xylose.

Figure 3:
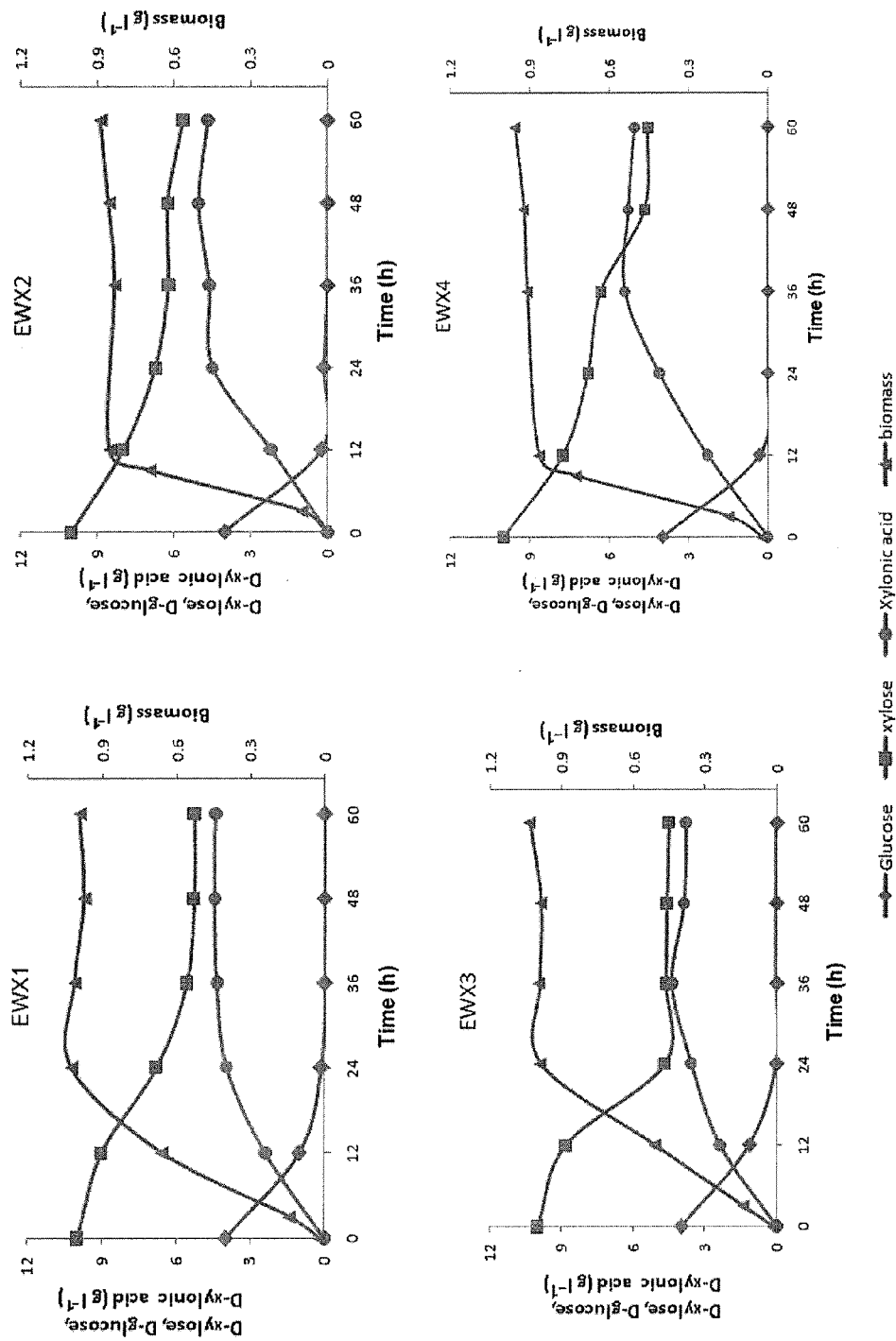
FIG. 3 shows graphs of productivity comparison by culturing *E. coli* W3110 (EWX1, EWX2 and EWX3 strains) to which dehydrogenase genes of *C. crescentus* are introduced in Example 1 of the present invention.

According to FIG. 3, accumulation of D-xylonic acid was found in all cultures of engineered strains. Trace amount of D-xylulose was detected transiently during the culture of EWX1 and EWX3 after D-glucose was exhausted, but was not detected in the strains EWX2 and EWX4.

No D-gluconic acid was found in any of the tested strains. Productivity and yield comparison among these strains indicated that EWX4 was the most efficient strain for blocking both the xylose and xylonic acid metabolic pathways.

After 60 hours of incubation with EWX4, 51% of D-xylose in the medium was converted to D-xylonic acid (5.05 g/L) with an average productivity of 84.23 mg/h.

HPLC analysis showed that 4.5 g/L of D-xylose remained in the culture. This implies that the increase of cell density would lead to high productivity.

As an enzyme activity assay, D-xylose dehydrogenase activity was measured from crude cell extracts. The protein concentration was determined using the Bio-Rad protein kit. One unit of D-xylose dehydrogenase activity is defined as the amount of enzyme that converted one μmol D-xylose to D-xylonic acid per minute, and the specific activity was calculated as enzyme activity per mg protein.

Further, biomass was measured as dry cell weight. Samples were transferred in 2 mL pre-dried and pre-weighed centrifuge tubes, pelleted at 14,000 rpm for 10 minutes, washed twice with distilled water and dried at 105° C. A standard curve of dry cell weight correlated to optical density at 600 nm ($OD_{600}$) was constructed; one $OD_{600}$ unit is equivalent to 0.32 g/L of cell dry weight.

As analyses of extracellular metabolites, extracellular metabolites such as D-glucose, D-glucuronic acid, D-xylose, D-xylulose and D-xylonic acid were analyzed by HPLC (column 300×8 mm) using 5 mM $H_2SO_4$ as eluent pumped at a flow rate of 0.4 mL/min.

The column temperature was maintained at 55° C. and peaks were detected using Waters 2414 refractive index detector. D-xylose could not be accurately determined using this HPLC method when D-xylonic acid was also present.

D-xylonic acid concentrations were also measured using a hydroxamate method. Samples were diluted in 0.7M HCl and boiled at 100° C. for 15 minutes to convert D-xylonic acid to xylono-γ-lactone before adding 500 μL of the diluted sample to 1 mL of hydroxylamine reagent (2M hydroxylamine HCl in 2M NaOH).

HCl (650 μl, 3.2M) was added, followed by addition of 500 μL of $FeCl_3$ (100 g/L in 0.1M HCl). Absorbance was measured immediately at 550 nm for D-xylonic acid quantification, which was then compared to the standard curve to determine the D-xylonic acid concentration. Since D-xylonic acid was the only reacting compound present in the supernatant, this assay was correlated well with HPLC measurements of D-xylonic acid.

EXAMPLE 5

D-Xylonic Acid Productivity in Laboratory Fermenter Scale

For larger scale fermentation experiments on *E. coli* EWX4, a 5 L-scale laboratory fermenter containing 3L M9 minimal salt, 10 g/L glucose and 40 g/L D-xylose was used for D-xylonic acid production.

In order to maintain xylose dehydrogenase expression during the fermentation, 0.5 mM ITPG was added for 24 hours after $OD_{600}$ reached 10. Strains continued growing by the addition of glucose.

Figure 4:
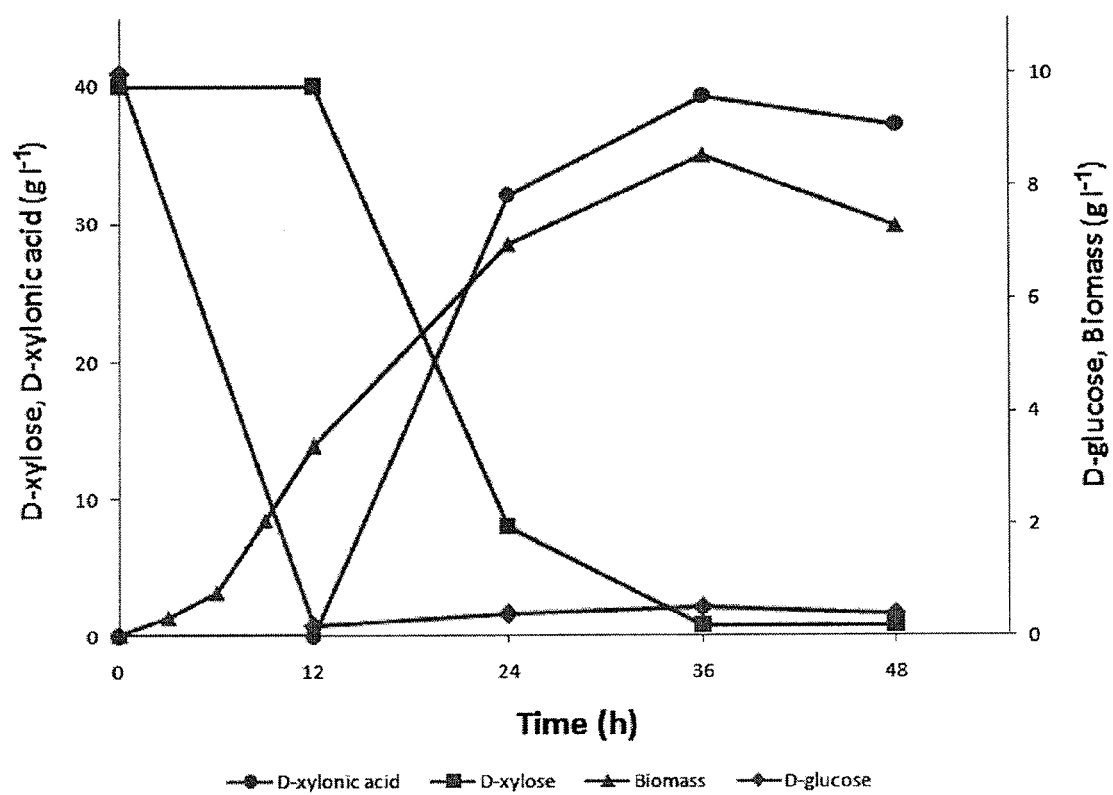
FIG. 4 shows D-xylonic acid productivity of *E. coli* EWX4 in a laboratory fermenter scale.

Results demonstrated that after 36 hours of fermentation, the highest concentration and yield of D-xylonic acid reached 39.21 g/L and 0.98 g D-xylonic acid/g D-xylose respectively, the specific productivity was 4.59 g xylonic acid/g biomass, and the highest productivity was 1.09 g $L^{-1}$ $h^{-1}$ The results are summarized in Table 4 and FIG. 4.

TABLE 4

| Incubation time (h) | D-xylonic acid concentration (g/l) | D-xylonic acid productivity (mg $L^{-1}h^{-1}$) | Yield (g [g D-xylose]$^{-1}$) |
|---|---|---|---|
| 24 | 32.02 | 1.33 | 0.80 |
| 36 | 39.21 | 1.09 | 0.98 |
| 48 | 37.21 | 0.78 | 0.93 |

*E. coli* has native metabolic pathways for both xylose and xylonic acid, but is incapable of converting xylose to xylonic acid. To render *E. coli* capable of producing xylonic acid, a xylose dehydrogenase gene of *C. crescentus* was introduced while both its xylose and xylonic acid catabolic pathways were blocked to prevent the conversion of xylose or xylonic acid to biomass.

Laboratory scale fermentation results indicated that xylonic acid was efficiently produced and accumulated in the culture of the engineered *E. coli* culture.

Up to 39.2 g/L D-xylonic acid was produced out of 40 g/L D-xylose when this strain was grown in a medium containing M9 minimal salt and glucose with average productivity of 1.09 g $L^{-1}$ $h^{-1}$.

Furthermore, no other byproducts such as glucuronic acid were found in the culture. These findings give this engineered strain more suitability for industrial-scale production of xylonic acid.

Figure 5:
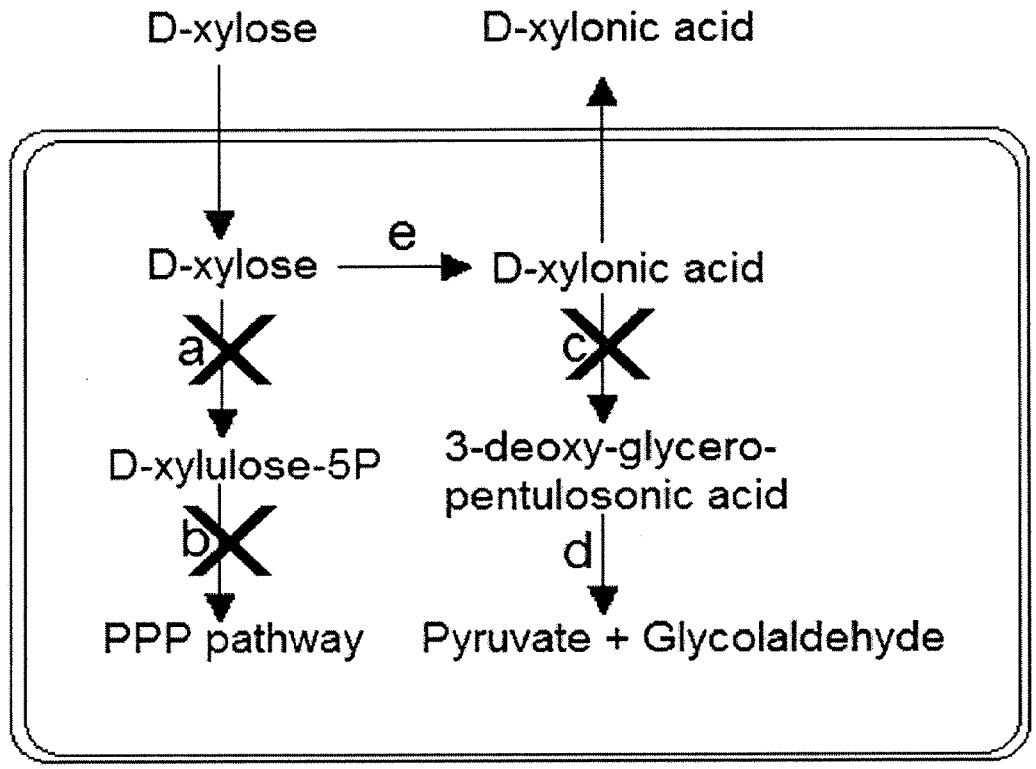
FIG. 5 shows a metabolic pathway of D-xylose and D-xylonic acid in the engineered *E. coli* EWX4 according to the present invention.

FIG. 5 illustrates the metabolic pathways of D-xylose and D-xylonic acid in the engineered *E. coli* EWX4 of the present invention wherein X indicates that the genes in EWX4 are disrupted.

The resulting xylonic acid productivity and yield of the engineered *E. coli* are both higher compared to the values reported using *Saccharomyces cerevisiae* or *Kluyveromyces lactis*.

The most important reason may be attributable to the transportation systems of the microorganism. *Saccharomyces cerevisiae* does not have transportation property of D-xylose while *Kluyveromyces lactis* have predicted to have transportation property. Neither *Saccharomyces cerevisiae* nor *Kluyveromyces lactis* is capable of utilizing D-xylonic acid as sole carbon source. This indicates that they do not have the property of transportation systems for xylonic acid in yeasts.

On the contrary, wild type *E. coli* W3110 can utilize both xylose and xylonic acid as a sole carbon source, suggesting the presence of transportation system for both compounds in *E. coli*. Therefore, neither xylose uptake nor xylonic acid secretion might be the limiting factor for xylonic acid production in engineered *E. coli*.

Although some embodiments have been described herein, it should be understood by those skilled in the art that these embodiments are given by way of illustration only, and that various modifications, variations, and alterations can be made without departing from the spirit and scope of the invention. Therefore, the scope of the invention should be limited only by the accompanying claims and equivalents thereof.

What is claimed is:

1. A recombinant *Escherichia coli* (*E. coli*) EWX4 (Microorganism deposition number KCTC11988BP) capable of producing D-xylonic acid from D-xylose.

* * * * *

SEQUENCE LISTING

<160> NUMBER OF SEQ ID NOS: 11

<210> SEQ ID NO 1
<211> LENGTH: 1323
<212> TYPE: DNA
<213> ORGANISM: Escherichia coli

<400> SEQUENCE: 1
atgcaagcct attttgacca gctcgatcgc gttcgttatg aaggctcaaa atcctcaaac    60
ccgttagcat tccgtcacta caatcccgac gaactggtgt tgggtaagcg tatggaagag   120

```
cacttgcgtt ttgccgcctg ctactggcac accttctgct ggaacggggc ggatatgttt      180
ggtgtggggg cgtttaatcg tccgtggcag cagcctggtg aggcactggc gttggcgaag      240
cgtaaagcag atgtcgcatt tgagtttttc cacaagttac atgtgccatt ttattgcttc      300
cacgatgtgg atgtttcccc tgagggcgcg tcgttaaaag agtacatcaa taattttgcg      360
caaatggttg atgtcctggc aggcaagcaa gaagagagcg gcgtgaagct gctgtgggga      420
acggccaact gctttacaaa ccctcgctac ggcgcgggtg cggcgacgaa cccagatcct      480
gaagtcttca gctgggcggc aacgcaagtt gttacagcga tggaagcaac ccataaattg      540
ggcggtgaaa actatgtcct gtggggcggt cgtgaaggtt acgaaacgct gttaaatacc      600
gacttgcgtc aggagcgtga acaactgggc cgctttatgc agatggtggt tgagcataaa      660
cataaaatcg gtttccaggg cacgttgctt atcgaaccga accgcaaga accgaccaaa      720 catcaatatg attacgatgc cgcgacggtc tatggcttcc tgaaacagtt tggtctggaa      780
aaagagatta aactgaacat tgaagctaac cacgcgacgc tggcaggtca ctctttccat      840
catgaaatag ccaccgccat tgcgcttggc ctgttcggtt ctgtcgacgc caaccgtggc      900
gatgcgcaac tgggctggga caccgaccag ttcccgaaca gtgtgaaga aatgcgctg       960 gtgatgtatg aaattctcaa agcaggcggt ttcaccaccg tggtctgaa cttcgatgcc      1020 aaagtacgtc gtcaaagtac tgataaatat gatctgtttt acggtcatat cggcgcgatg      1080
gatacgatgg cactggcgct gaaaattgca gcgcgcatga ttgaagatgg cgagctggat      1140
aaacgcatcg cgcagcgtta ttccggctgg aatagcgaat gggccagca atcctgaaa       1200 ggccaaatgt cactggcaga tttagccaaa tatgctcagg aacatcattt gtctccggtg      1260
catcagagtg gtcgccagga acaactggaa atctggtaa accattatct gttcgacaaa      1320
taa                                                                    1323

<210> SEQ ID NO 2
<211> LENGTH: 1455
<212> TYPE: DNA
<213> ORGANISM: Escherichia coli

<400> SEQUENCE: 2
atgtatatcg ggatagatct tggcacctcg ggcgtaaaag ttattttgct caacgagcag       60
ggtgaggtgg ttgctgcgca acggaaaag ctgaccgttt cgcgcccgca tccactctgg      120
tcggaacaag acccggaaca gtggtggcag gcaactgatc gcgcaatgaa agctctgggc      180
gatcagcatt ctctgcagga cgttaaagca ttgggtattg ccggccagat gcacggagca      240
accttgctgg atgctcagca acgggtgtta cgccctgcca ttttgtggaa cgacgggcgc      300
tgtgcgcaag agtgcacttt gctggaagcg cgagttccgc aatcgcgggt gattaccggc      360
aacctgatga tgcccggatt tactgcgcct aaattgctat gggttcagcg gcatgagccg      420
gagatattcc gtcaaatcga caaagtatta ttaccgaaag attacttgcg tctgcgtatg      480 acggggagt ttgccagcga tatgtctgac gcagctggca ccatgtggct ggatgtcgca      540
aagcgtgact ggagtgacgt catgctgcag gcttgcgact atctcgtga ccagatgccc       600 gcattatacg aaggcagcga aattactggt gctttgttac ctgaagttgc gaaagcgtgg      660
ggtatggcga cggtgccagt tgtcgcaggc ggtggcgaca atgcagctgg tgcagttggt      720
gtgggaatgg ttgatgctaa tcaggcaatg ttatcgctgg ggacgtcggg ggtctatttt      780
gctgtcagcg aagggttctt aagcaagcca gaaagcgccg tacatagctt tgccatgcg       840 ctaccgcaac gttggcattt aatgtctgtg atgctgagtg cagcgtcgtg tctggattgg      900
```

-continued

```
gccgcgaaat taaccggcct gagcaatgtc ccagctttaa tcgctgcagc tcaacaggct    960
gatgaaagtg ccgagccagt ttggtttctg ccttatcttt ccggcgagcg tacgccacac   1020
aataatcccc aggcgaaggg ggttttcttt ggtttgactc atcaacatgg ccccaatgaa   1080
ctggcgcgag cagtgctgga aggcgtgggt tatgcgctgg cagatggcat ggatgtcgtg   1140
catgcctgcg gtattaaacc gcaaagtgtt acgttgattg ggggcggggc gcgtagtgag   1200
tactggcgtc agatgctggc ggatatcagc ggtcagcagc tcgattaccg tacggggggg   1260
gatgtggggc cagcactggg cgcagcaagg ctggcgcaga tcgcggcgaa tccagagaaa   1320
tcgctcattg aattgttgcc gcaactaccg ttagaacagt cgcatctacc agatgcgcag   1380
cgttatgccg cttatcagcc acgacgagaa acgttccgtc gcctctatca gcaacttctg   1440
ccattaatgg cgtaa                                                    1455

<210> SEQ ID NO 3
<211> LENGTH: 930
<212> TYPE: DNA
<213> ORGANISM: Escherichia coli

<400> SEQUENCE: 3
atgattcagc aaggagatct catgccgcag tccgcgttgt tcacgggaat cattccccct     60
gtctccacca tttttaccgc cgacggccag ctcgataagc cgggcaccgc cgcgctgatc    120
gacgatctga tcaaagcagg cgttgacggc ctgttcttcc tgggcagcgg tggcgagttc    180
tcccagctcg gcgccgaaga gcgtaaagcc attgcccgct ttgctatcga tcatgtcgat    240
cgtcgcgtgc cggtgctgat cggcaccggc ggcaccaacg cccgggaaac catcgaactc    300
agccagcacg cgcagcaggc gggcgcggac ggcatcgtgg tgatcaaccc ctactactgg    360
aaagtgtcgg aagcgaacct gatccgctat ttcgagcagg tggccgacag cgtcacgctg    420
ccggtgatgc tctataactt cccggcgctg accgggcagg atctgactcc ggcgctggtg    480
aaaaccctcg ccgactcgcg cagcaatatt atcggcatca agacaccat cgactccgtc    540 gcccacctgc gcagcatgat ccataccgtc aaaggtgccc atccgcactt caccgtgctc    600
tgcggctacg acgatcatct gttcaatacc ctgctgctcg gcggcgacgg ggcgatatcg    660
gcgagcggca actttgcccc gcaggtgtcg gtgaatcttc tgaaagcctg gcgcgacggg    720
gacgtggcga agcggccgg gtatcatcag accttgctgc aaattccgca gatgtatcag    780
ctggatacgc cgtttgtgaa cgtgattaaa gaggcgatcg tgctctgcgg tcgtcctgtc    840
tccacgcacg tgctgccgcc cgcctcgccg ctggacgagc cgcgcaaggc gcagctgaaa    900
accctgctgc aacagctcaa gctttgctga                                     930

<210> SEQ ID NO 4
<211> LENGTH: 936
<212> TYPE: DNA
<213> ORGANISM: Escherichia coli

<400> SEQUENCE: 4
atgagcactt acgaaaagga aactgaggta atgaaaaaat tcagcggcat tattccaccg     60
gtatccagca cgtttcatcg tgacggaacc cttgataaaa aggcaatgcg cgaagttgcc    120
gacttcctga ttaataaagg ggtcgacggg ctgttttatc tgggtaccgg tggtgaattt    180
agccaaatga atacagccca gcgcatggca ctcgccgaag aagctgtaac cattgtcgac    240
gggcgagtgc cggtattgat tggcgtcggt tccccttcca ctgacgaagc ggtcaaactg    300
gcgcagcatg cgcaagccta cggcgctgat ggtatcgtcg ccatcaaccc ctactactgg    360
```

```
aaagtcgcac cacgaaatct tgacgactat taccagcaga tcgcccgtag cgtcacccta    420
ccggtgatcc tgtacaactt tccggatctg acgggtcagg acttaacccc ggaaaccgtg    480
acgcgtctgg ctctgcaaaa cgagaatatc gttggcatca agacaccat  cgacagcgtt   540 ggtcacttgc gtacgatgat caacacagtt aagtcggtac gcccgtcgtt ttcggtattc    600
tgcggttacg atgatcattt gctgaatacg atgctgctgg cggcgacgg  tgcgataacc   660 gccagcgcta actttgctcc ggaactctcc gtcggcatct accgcgcctg gcgtgaaggc    720
gatctggcga ccgctgcgac gctgaataaa aaactactac aactgcccgc tatttacgcc    780
ctcgaaacac cgtttgtctc actgatcaaa tacagcatgc agtgtgtcgg gctgcctgta    840
gagacatatt gcttaccacc gattcttgaa gcatctgaag aagcaaaaga taaagtccac    900
gtgctgctta ccgcgcaggg cattttacca gtctga                             936

<210> SEQ ID NO 5
<211> LENGTH: 61
<212> TYPE: DNA
<213> ORGANISM: Artificial Sequence
<220> FEATURE:
<223> OTHER INFORMATION: KxylAB-F Primer

<400> SEQUENCE: 5
tcgtgaaggt tacgaaacgc tgttaaatac cgacttgcgt catatgaata tcctccttag    60
t                                                                    61

<210> SEQ ID NO 6
<211> LENGTH: 61
<212> TYPE: DNA
<213> ORGANISM: Artificial Sequence
<220> FEATURE:
<223> OTHER INFORMATION: KxylAB-R Primer

<400> SEQUENCE: 6
cggctcatgc cgctgaaccc atagcaattt aggcgcagta gtgtaggctg gagctgcttc    60
g                                                                    61

<210> SEQ ID NO 7
<211> LENGTH: 61
<212> TYPE: DNA
<213> ORGANISM: Artificial Sequence
<220> FEATURE:
<223> OTHER INFORMATION: KyihG-F Primer

<400> SEQUENCE: 7
gtgcaaacca ttggcgcacg cttcgccaat ggcgaattat gtgtaggctg gagctgcttc    60
g                                                                    61

<210> SEQ ID NO 8
<211> LENGTH: 61
<212> TYPE: DNA
<213> ORGANISM: Artificial Sequence
<220> FEATURE:
<223> OTHER INFORMATION: KyihG-R Primer

<400> SEQUENCE: 8
gtgcaaacca ttggcgcacg cttcgccaat ggcgaattat gtgtaggctg gagctgcttc    60
g                                                                    61

<210> SEQ ID NO 9
<211> LENGTH: 60
```

```
<212> TYPE: DNA
<213> ORGANISM: Artificial Sequence
<220> FEATURE:
<223> OTHER INFORMATION: KyagF-F Primer

<400> SEQUENCE: 9
cgccaccatg attgcgctgg ccgcgatgca cgacctgccg atatgaatat cctccttagt    60

<210> SEQ ID NO 10
<211> LENGTH: 61
<212> TYPE: DNA
<213> ORGANISM: Artificial Sequence
<220> FEATURE:
<223> OTHER INFORMATION: KyagF-R Primer

<400> SEQUENCE: 10
cctgctcgcg caggcactgg cggaagcgcg cccggcgctc gtgtaggctg gagctgcttc    60
g                                                                    61

<210> SEQ ID NO 11
<211> LENGTH: 747
<212> TYPE: DNA
<213> ORGANISM: Caulobacter crescentus

<400> SEQUENCE: 11
atgtcctcag ccatctatcc cagcctgaag ggcaagcgcg tcgtcatcac cggcggcggc    60
tcgggcatcg gggccggcct caccgccggc ttcgcccgtc agggcgcgga ggtgatcttc   120
ctcgacatcg ccgacgagga ctccagggct cttgaggccg agctggccgg ctcgccgatc   180
ccgccggtct acaagcgctg cgacctgatg aacctcgagg cgatcaaggc ggtcttcgcc   240
gagatcggcg acgtcgacgt gctggtcaac aacgccggca tgacgaccg ccacaagctg   300
gccgacgtga ccggcgccta ttgggacgag cggatcaacg tcaacctgcg ccacatgctg   360
ttctgcaccc aggccgtcgc gccgggcatg aagaagcgtg gcggcgggc ggtgatcaac   420
ttcggttcga tcagctggca cctggggctt gaggacctcg tcctctacga aaccgccaag   480
gccggcatca aggcatgac ccgcgcgctg gcccgggagc tgggtcccga cgacatccgc   540
gtcacctgcg tggtgccggg caacgtcaag accaagcgcc aggagaagtg gtacacgccc   600
gaaggcgagg cccagatcgt ggcggcccaa tgcctgaagg gccgcatcgt cccggagaac   660
gtcgccgcgc tggtgctgtt cctggcctcg gatgacgcgt cgctctgcac cggccacgaa   720
tactggatcg acgccggctg gcgttga                                        747
```